US009078677B2

(12) United States Patent
Trees et al.

(10) Patent No.: US 9,078,677 B2
(45) Date of Patent: Jul. 14, 2015

(54) SURGICAL INSTRUMENT WITH CURVED BLADE FIRING PATH

(71) Applicant: Ethicon Endo-Surgery, Inc., Cincinnati, OH (US)

(72) Inventors: Gregory A. Trees, Loveland, OH (US); Bingshi Wang, Mason, OH (US); Nathaniel F. Barbera, Somerset, PA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 212 days.

(21) Appl. No.: 13/692,202

(22) Filed: Dec. 3, 2012

(65) Prior Publication Data

US 2014/0155878 A1    Jun. 5, 2014

(51) Int. Cl.
*A61B 18/18* (2006.01)
*A61B 17/295* (2006.01)
*A61B 17/29* (2006.01)
*A61B 18/14* (2006.01)

(52) U.S. Cl.
CPC ............... *A61B 18/18* (2013.01); *A61B 17/295* (2013.01); *A61B 2017/2945* (2013.01); *A61B 2018/1452* (2013.01); *A61B 2018/1455* (2013.01); *A61B 2018/1457* (2013.01)

(58) Field of Classification Search
CPC .................. A61B 17/295; A61B 18/18; A61B 2017/2945; A61B 2018/1452; A61B 2018/1455; A61B 2018/1457
USPC .......................................................... 606/51
See application file for complete search history.

(56) References Cited

U.S. PATENT DOCUMENTS

| 4,316,468 | A | * | 2/1982 | Klieman et al. | ............... 606/143 |
| 5,156,315 | A | | 10/1992 | Green et al. | |
| 5,779,701 | A | * | 7/1998 | McBrayer et al. | ............... 606/46 |
| 6,500,176 | B1 | | 12/2002 | Truckai et al. | |
| 6,783,524 | B2 | | 8/2004 | Anderson et al. | |
| 6,966,909 | B2 | * | 11/2005 | Marshall et al. | ................ 606/41 |
| 7,112,201 | B2 | | 9/2006 | Truckai et al. | |
| 7,125,409 | B2 | | 10/2006 | Truckai et al. | |
| 7,169,146 | B2 | | 1/2007 | Truckai et al. | |
| 7,186,253 | B2 | | 3/2007 | Truckai et al. | |
| 7,189,233 | B2 | | 3/2007 | Truckai et al. | |
| 7,220,951 | B2 | | 5/2007 | Truckai et al. | |
| 7,309,849 | B2 | | 12/2007 | Truckai et al. | |

(Continued)

FOREIGN PATENT DOCUMENTS

| EP | 1943960 | 7/2008 |
| EP | 2165661 | 3/2010 |
| EP | 2223661 | 9/2010 |

OTHER PUBLICATIONS

U.S. Appl. No. 13/749,889, filed Jan. 25, 2013, Worrell et al.

(Continued)

*Primary Examiner* — George Manuel
(74) *Attorney, Agent, or Firm* — Frost Brown Todd LLC

(57) ABSTRACT

An apparatus includes an end effector having a first jaw and a second jaw. The first and second jaws are able to clamp tissue. The first jaw and the second jaw define a curved path. The apparatus further includes a blade that is operable to translate along a curved path in the end effector. At least a portion of the blade is precurved. The blade may further include a laminate of sheets that slide relative to each other to accommodate travel along the curved path.

20 Claims, 12 Drawing Sheets

(56) References Cited

U.S. PATENT DOCUMENTS

| | | |
|---|---|---|
| 7,311,709 B2 | 12/2007 | Truckai et al. |
| 7,354,440 B2 | 4/2008 | Truckal et al. |
| 7,381,209 B2 | 6/2008 | Truckai et al. |
| 7,909,823 B2 | 3/2011 | Moses et al. |
| 7,988,028 B2 | 8/2011 | Farascioni et al. |
| 8,893,949 B2 | 11/2014 | Shelton et al. |
| 2002/0111624 A1* | 8/2002 | Witt et al. ............ 606/51 |
| 2011/0087218 A1 | 4/2011 | Boudreaux et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |

OTHER PUBLICATIONS

U.S. Appl. No. 61/410,603, filed Nov. 5, 2010, Houser.
International Search Report dated Sep. 15, 2014 for Application No. PCT/US2013/072636, 8 pages.
International Written Opinion dated Sep. 15, 2014 for Application No. PCT/US2013/072636, 7 pages.

* cited by examiner

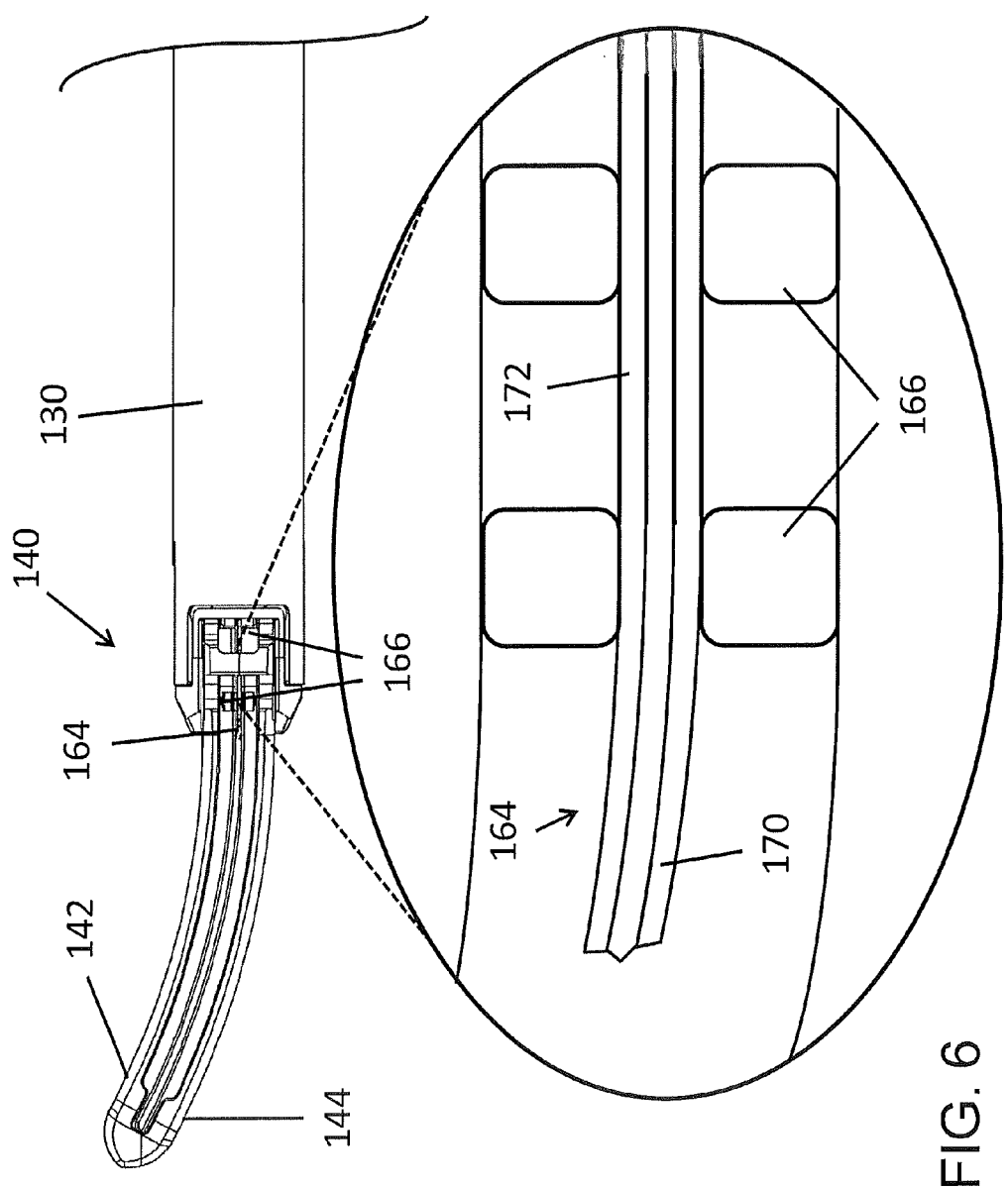

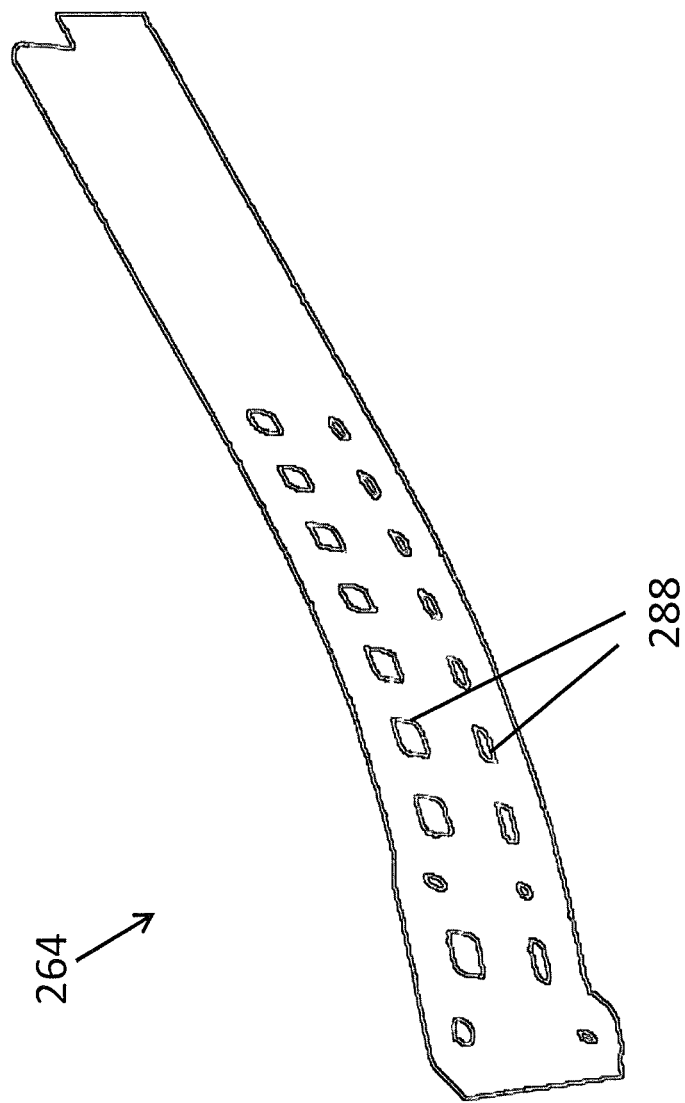

SURGICAL INSTRUMENT WITH CURVED BLADE FIRING PATH

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. patent application Ser. No. 13/622,729, entitled "Surgical Instrument with Multi-Phase Trigger Bias," filed Sep. 19, 2012 and published Jan. 31, 2013 (U.S. Pub. No. 2013/0030428), the disclosure of which is incorporated by reference herein; and U.S. patent application Ser. No. 13/622,735, entitled "Surgical Instrument with Contained Dual Helix Actuator Assembly," filed Sep. 19, 2012 and published Jan. 24, 2013 (Pub. No. 2013/0023868), the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts an enlarged top plan view of the blade of the end effector of FIG. 5A;

FIG. 7 depicts a perspective view of an alternative exemplary blade;

Figure 1:
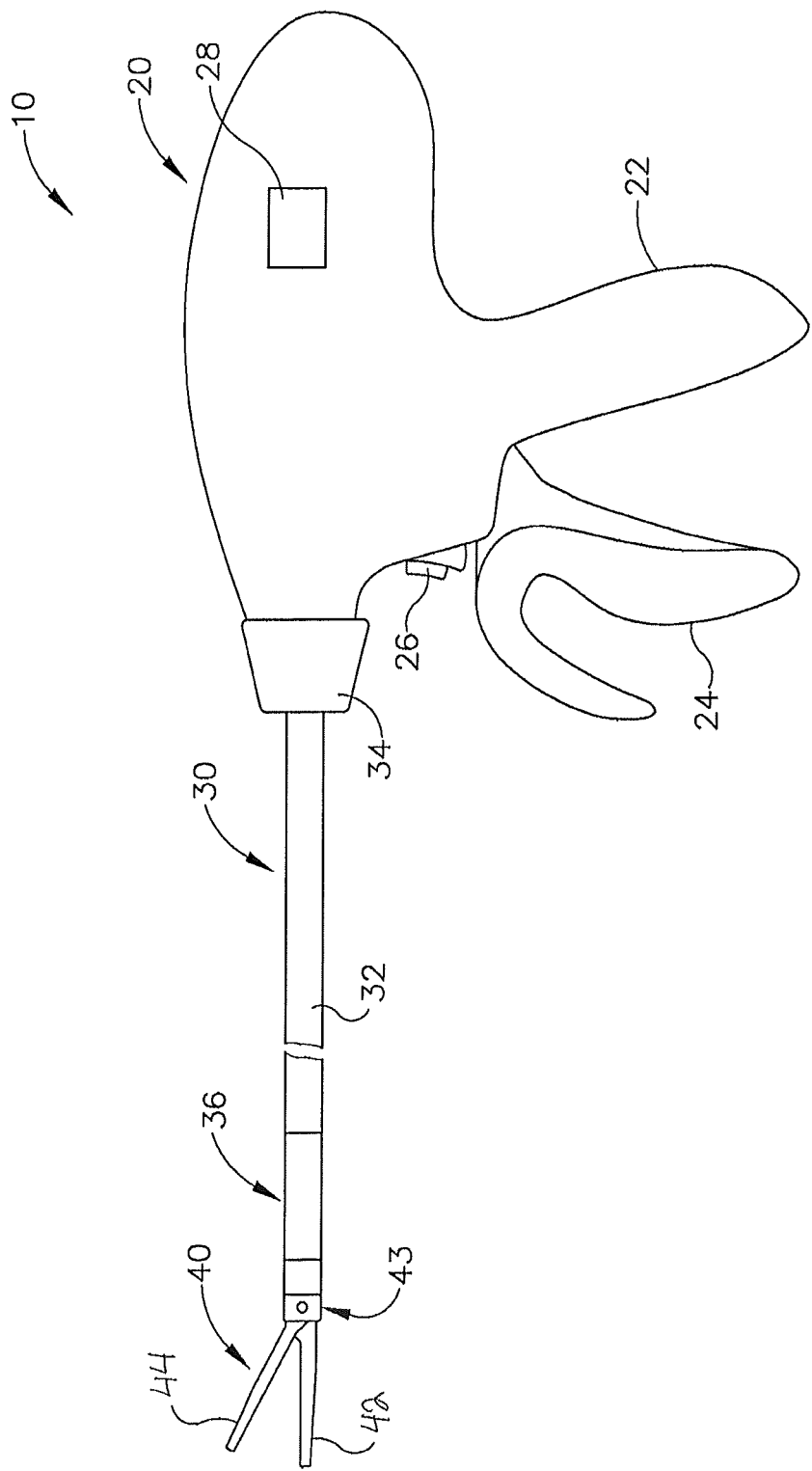
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0116379; U.S. Pub. No. 2012/0078243; U.S. Pub. No. 2012/0078247; U.S. Pub. No. 2013/0030428; and/or U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
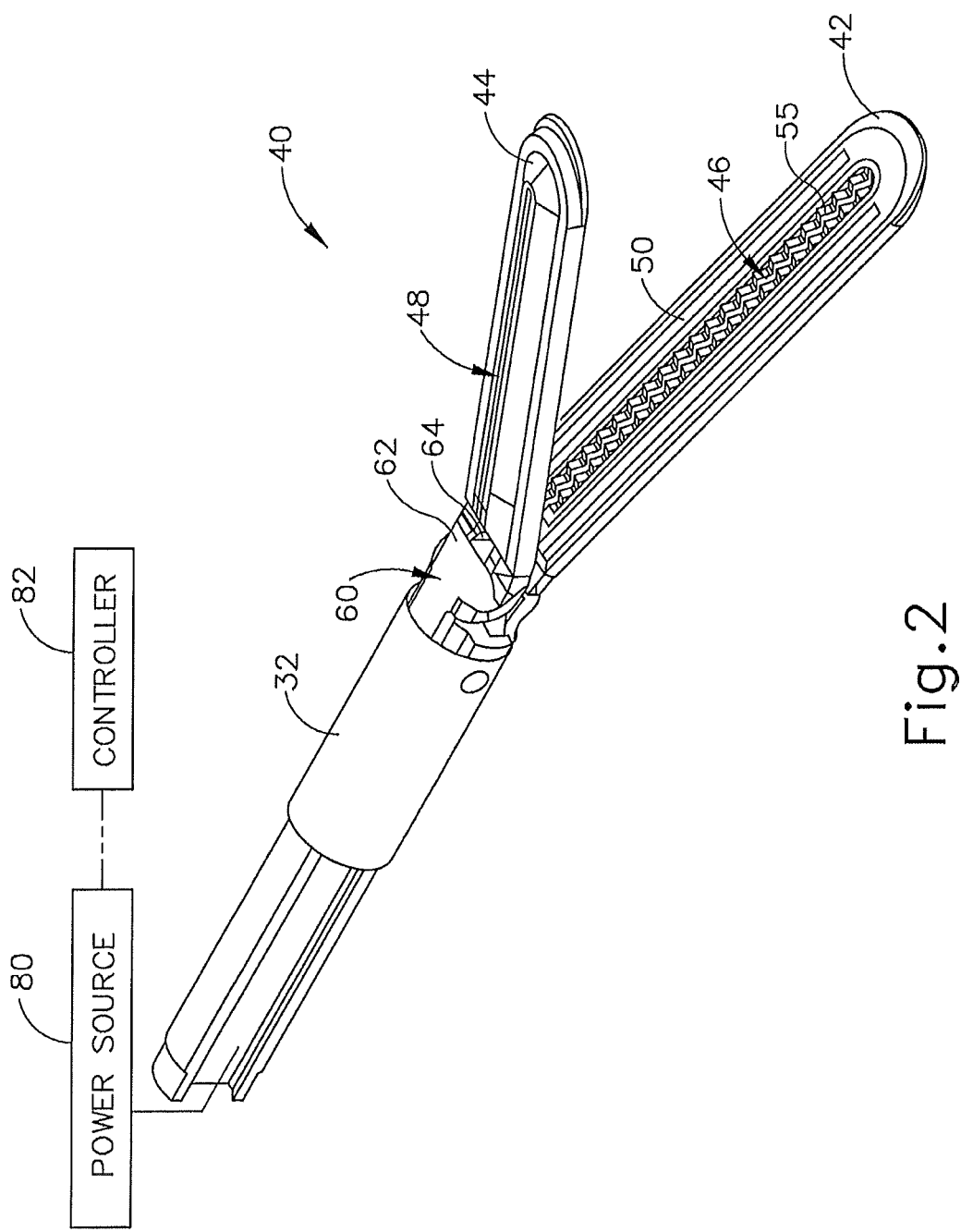
FIG. 2 depicts a perspective view of the end effector of the instrument of FIG. 1, in an open configuration.
Figure 3:
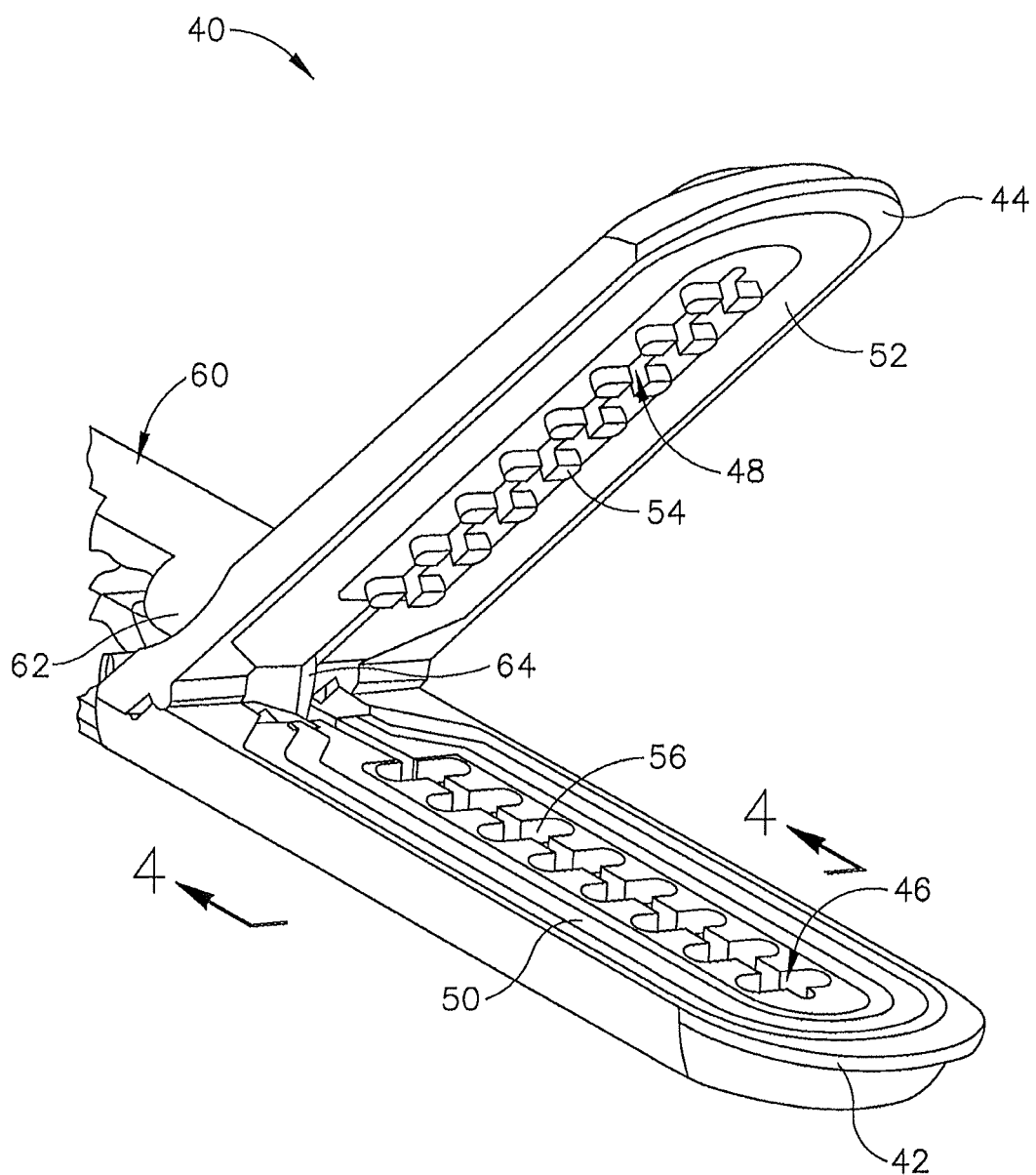
FIG. 3 depicts another perspective view of the end effector of the instrument of FIG. 1, in an open configuration.
Figure 4:
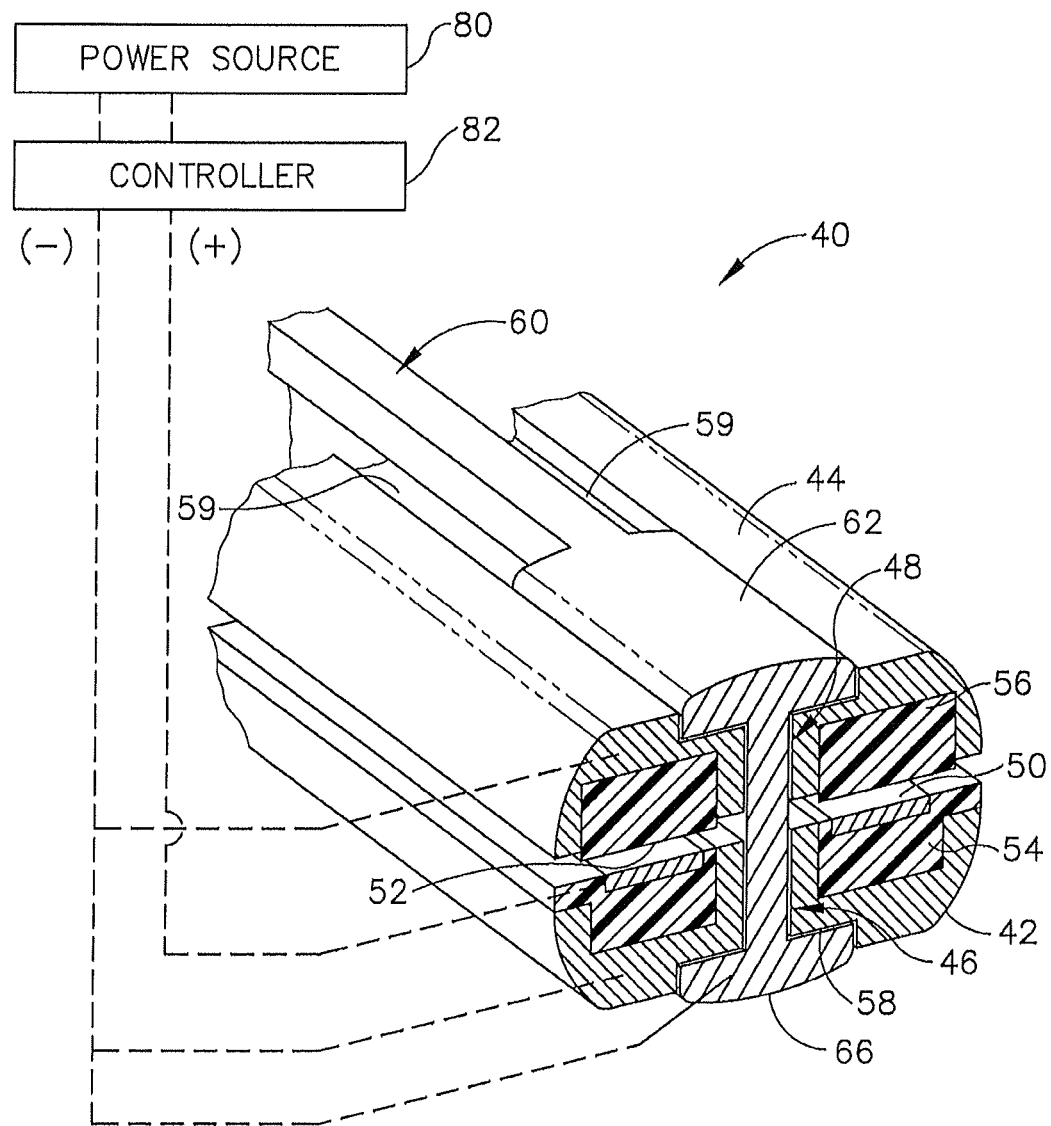
FIG. 4 depicts a cross-sectional end view of the end effector of FIG. 2 taken along line 4-4 of FIG. 3, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Curved End Effector

As described above, instrument (10) may be used to clamp, cut, and seal tissue. FIG. 2 showed end effector (40) with a generally straight shape. In particular, jaws (42, 44) have a straight, elongated form. Accordingly, blade (64) transects in a straight path along the length of jaws (42, 44). It will be understood that a straight end effector (40) may be useful in situations where end effector (40) needs to be inserted into a surgical area able to accept a straight end effector (40). In some instances, the user may prefer a straight end effector (40) for the particular operation being performed. In other instances, it will be appreciated that it may be desirable to use an end effector having a curved or otherwise bent shape, such that the distal end of end effector (40) is laterally offset from the longitudinal axis of shaft (30) while the proximal end of end effector (40) is generally parallel to the longitudinal axis of shaft (30). For instance, the arrangement of anatomical structures in the surgical field may warrant use of a curved version of end effector (40), such as in order to reach around an anatomical structure to more easily reach target tissue with end effector (40). It should also be understood that a curved version of end effector (40) may provide improved visualization of tissue that is to be transected.

Figure 5A:
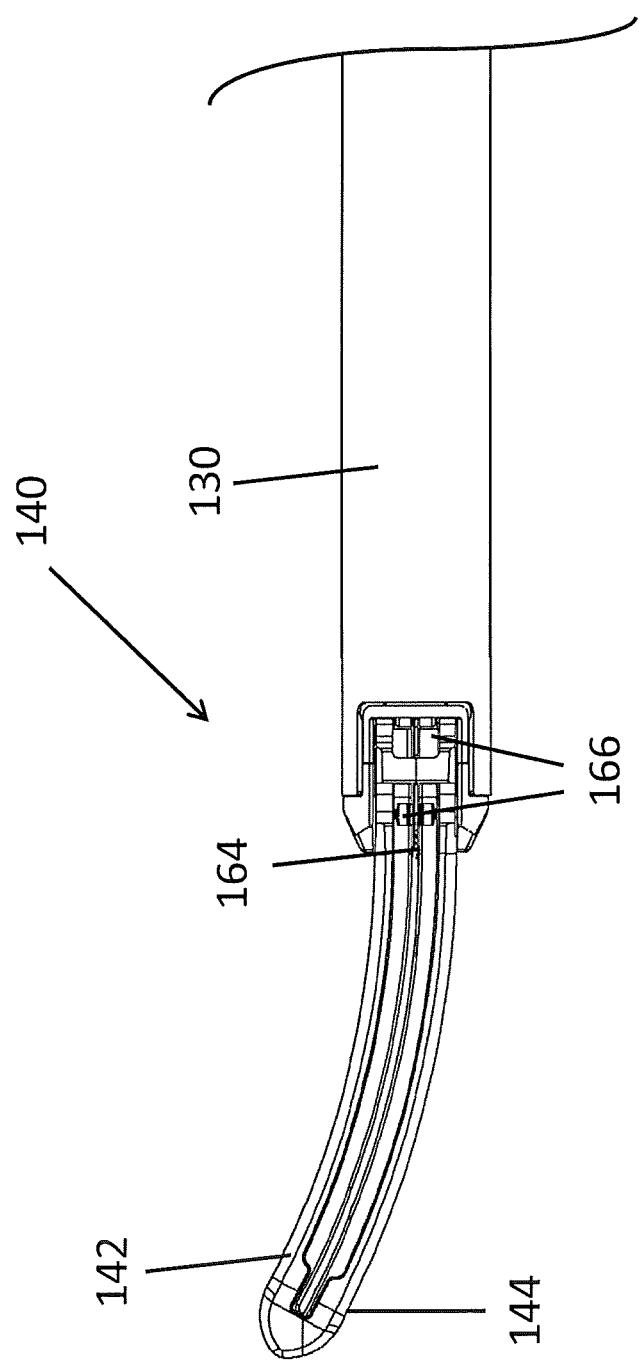
FIG. 5A depicts a top, plan view of an alternative exemplary end effector with a curved jaw, with a blade at a proximal position.

FIGS. 5A-6 depict an exemplary end effector (140) for use with a surgical instrument such as instrument (10) shown in FIG. 1. End effector (140) is connected to shaft (130). It will be understood that shaft (130) is substantially similar to shaft (30) shown in FIG. 1. It will be further understood that shaft (130) leads to a knob (34) and hand piece (20) such as those shown in FIG. 1. End effector (140) is generally substantially similar to end effector (40) of FIG. 1.

End effector (140) comprises a first jaw (142), a second jaw (144), and a blade (164) that advances along jaws (142, 144) with pins (166). In particular, a firing beam similar to firing beam (60) shown in FIG. 2 advances along end effector (140) along jaws (142, 144). As the firing beam advances, first jaw (142) is closed against second jaw (144). Pins (166) are coupled to blade (164) such that as pins (166) advance, pins (166) advance blade (164) distally along jaws (142, 144). Furthermore, as blade (164) advances along end effector (140), pins (166) travel along jaws (142, 144) with the firing beam (such as one shown in FIG. 2) to clamp jaws (142, 144) onto tissue. Pins (166) are thus substantially similar to flanges (62, 64) described above. It will be understood that pins (166) and blade (164) may be separate components as shown in FIG. 6, or in the alternative, pins (166) and blade (164) may have a single unitary construction. Furthermore, it will be appreciated that blade (164) and pins (166) may be integrated into a single piece blade. In yet other versions, other features of firing rod (60) shown in FIG. 2 may be integrated or formed as a single piece with blade (164). For instance, pins (166) and flange (62) may be integrated with blade (164) to form a single blade having both pins and flanges. Other suitable variations will be apparent to one of ordinary skill in the art.

Figure 5B:
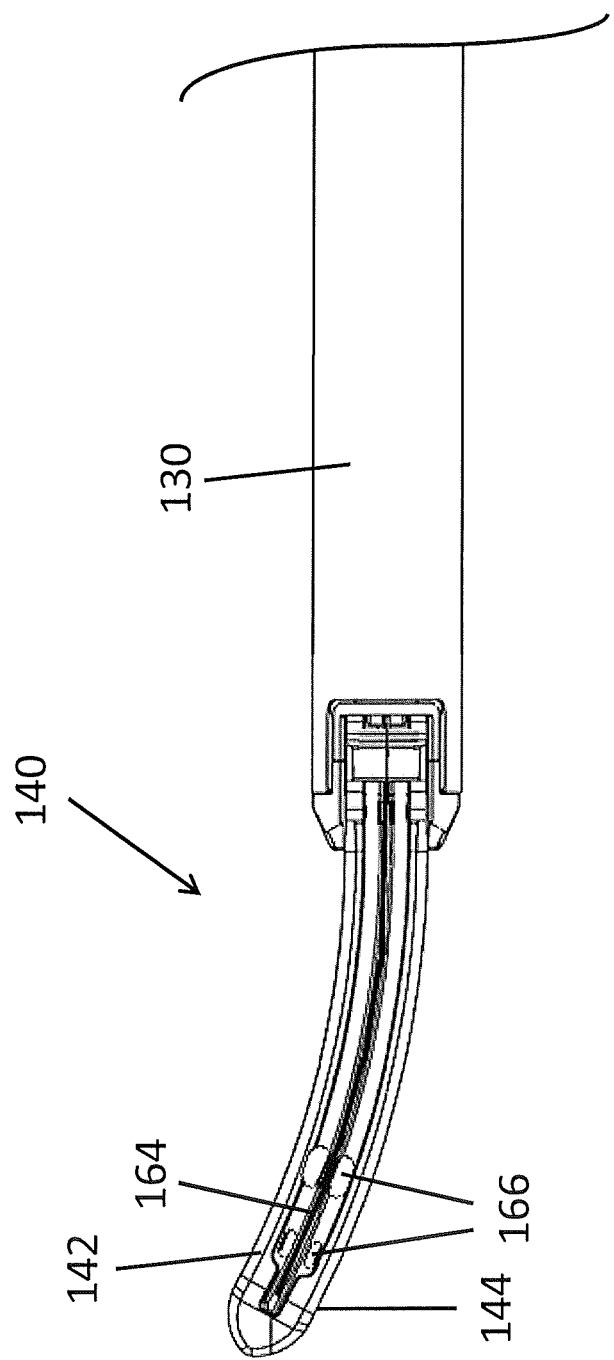
FIG. 5B depicts a top, plan view of the end effector of FIG. 5A, with the blade distally advanced.

FIG. 5B shows pins (166) advanced along end effector (140) with blade (164) advanced in a distal position. As described above with respect to FIGS. 2-3, blade (64) advances to cut tissue. Similarly, blade (164) of FIGS. 5A-5B may advance to cut tissue.

End effector (140) of the exemplary version has a curved shape as seen in FIG. 5A. The shape of end effector (140) in FIG. 5A curves to the right, but it will be understood that end effector (140) may instead curve to the left rather than the right. Furthermore, end effector (140) may curve in a more shallow or more steep manner. It will be understood that end effector (140) may curve in any suitable manner as would be apparent to one of ordinary skill in the art in view of the teachings herein.

Since end effector (140) is curved, it may be desirable for blade (164) to be curved as well. Blade (164), which can be seen enlarged in FIG. 6 is pre-curved in the present example, such that blade (164) is resiliently biased to assume a curved configuration. Blade (164) comprises a proximal portion (172) and a distal portion (170). As was seen in FIGS. 5A-5B, blade (164) is movable between a retracted state (FIG. 5A) and an advanced state (FIG. 5B). In FIG. 6, blade (164) is in a retracted state, and when blade (164) is in a retracted state, proximal portion (172) extends through pins (166) to meet with distal portion (170), which is positioned just distal to pins (166). Proximal portion (172) comprises a straight blade, whereas distal portion (170) comprises a pre-curved blade as seen in FIG. 6. However, it will be understood that both proximal portion (172) and distal portion (170) may comprise a pre-curved blade. In yet other versions, perhaps proximal portion (172) comprises a pre-curved blade whereas distal portion (170) comprises a straight blade. In the exemplary version, distal portion (170) has a length of about ½ inch. Longer and shorter lengths for distal portion (170) may nevertheless be used. Furthermore, distal portion (170) is pre-curved to generally match the curvature of jaw (142). Alternatively, the curvature of distal portion (170) of blade (164) may be greater or less than the curvature of jaws (142, 144). Other suitable variations for shaping proximal portion (172) and distal portion (170) will be apparent to one of ordinary skill in the art in view of the teachings herein. It will be appreciated that the pre-curved shape of distal portion (170) enables blade (164) to translate along jaws (142, 144) without cutting into, galling, or otherwise significantly dragging against the sides of jaws (142, 144). Accordingly, it will be appreciated that the pre-curved shape of distal portion (170) may reduce friction or interference during advancement of blade (164), thereby resulting in less force being required to advance blade (164). In a similar manner, the pre-curved shape of distal portion (170) may also reduce force required to retract blade (164) from a distal position.

Furthermore, in the illustrated version, blade (164) comprises layered metal to form blade (164). Further details on how a blade (164) may be formed of layers will be described in greater detail below. While the exemplary version shows three layers for blade (164) it will be appreciated that any suitable number of layers, including a single layer, may be used as would be apparent to one of ordinary skill in the art in view of the teachings herein. In some versions, it will also be understood that blade (164) may be coated and/or constructed of a stainless steel or a spinodal bronze. In other versions, however, any suitable material for blade (164) or a coating for blade (164) may be used as would be apparent to one of ordinary skill in the art in view of the teachings herein.

III. Exemplary Laminate Blade

Figure 8:
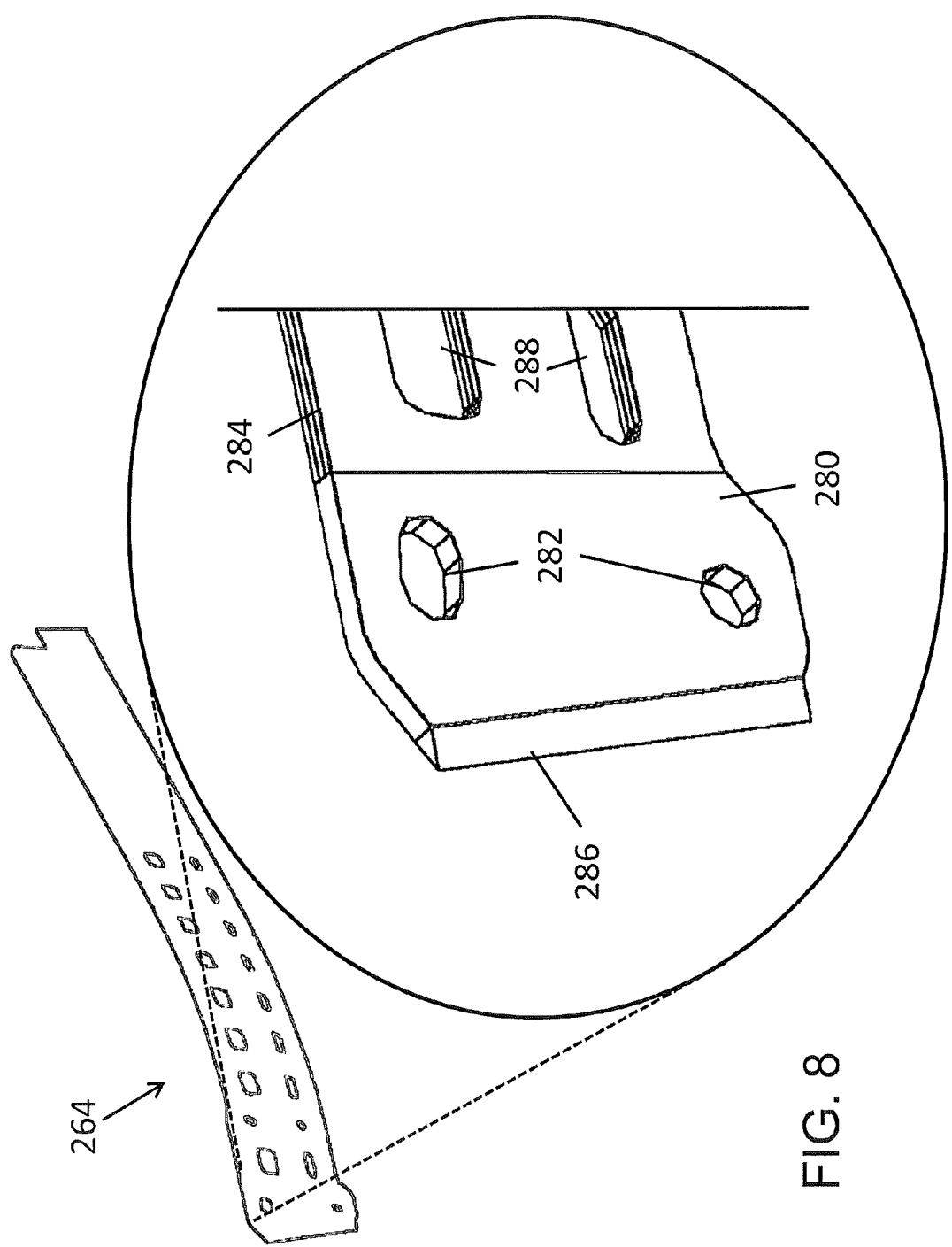
FIG. 8 depicts an enlarged perspective view of the blade of FIG. 7.

FIGS. 5A-6 show one exemplary blade (164) that may be used to translate through a curved end effector (140) such as the one shown in FIG. 5A. However, FIGS. 7-9B show an alternative blade (264) that may be used, for instance, instead of blade (164). Turning to FIG. 8, which shows an enlarged view of blade (264), blade (264) of this example comprises a head (280), an edge (286), a body (284), and pin holes (282). Blade (264) of FIG. 7 may be operable to be used interchangeably with blade (64) of FIG. 2-3 or with blade (164) shown in FIG. 6. For instance, pins (166) may be inserted through pin holes (282) to secure blade (264) for use with end effector (140). Thereafter, it will be appreciated that end effector (140) can carry out its normal mode of operation using blade (264) to transect tissue clamped between jaws (142, 144).

Edge (286) is positioned at the distal end of blade (264). Edge (286) comprises a sharp member that extends substantially the vertical distance of the height of blade (264). It will be understood that edge (286) may extend for a portion of the vertical distance of the height of blade (264) or any other suitable distance as would be apparent to one of ordinary skill in the art in view of the teachings herein. Furthermore, edge (286) has a generally straight and uniform profile throughout the length of edge (286), but it will be understood that edge (286) may have any suitable shape. For instance, edge (286) may have a jagged or serrated or a curved profile. Other suitable profiles for edge (286) will be apparent to one of ordinary skill in the art in view of the teachings herein.

Edge (286) is an integral, unitary feature of head (280). Head (280) in the exemplary version comprises a solid metal such as stainless steel or any other suitable solid metal. In the present example, edge (286) is formed by grinding the distal end of head (280), though it should be understood that edge (286) may be formed in various other ways. Head (280) further defines pin holes (282) formed in head (280). While pin holes (282) are shown in the exemplary version, it will be understood that in some cases, pin holes (282) may be omitted. Head (280) connects to body (284). Head (280) and body (284) may be flexibly welded together. In other versions, head (280) and body (284) may be connected in any suitable manner as would be apparent to one of ordinary skill in the art in view of the teachings herein.

Figure 9A:
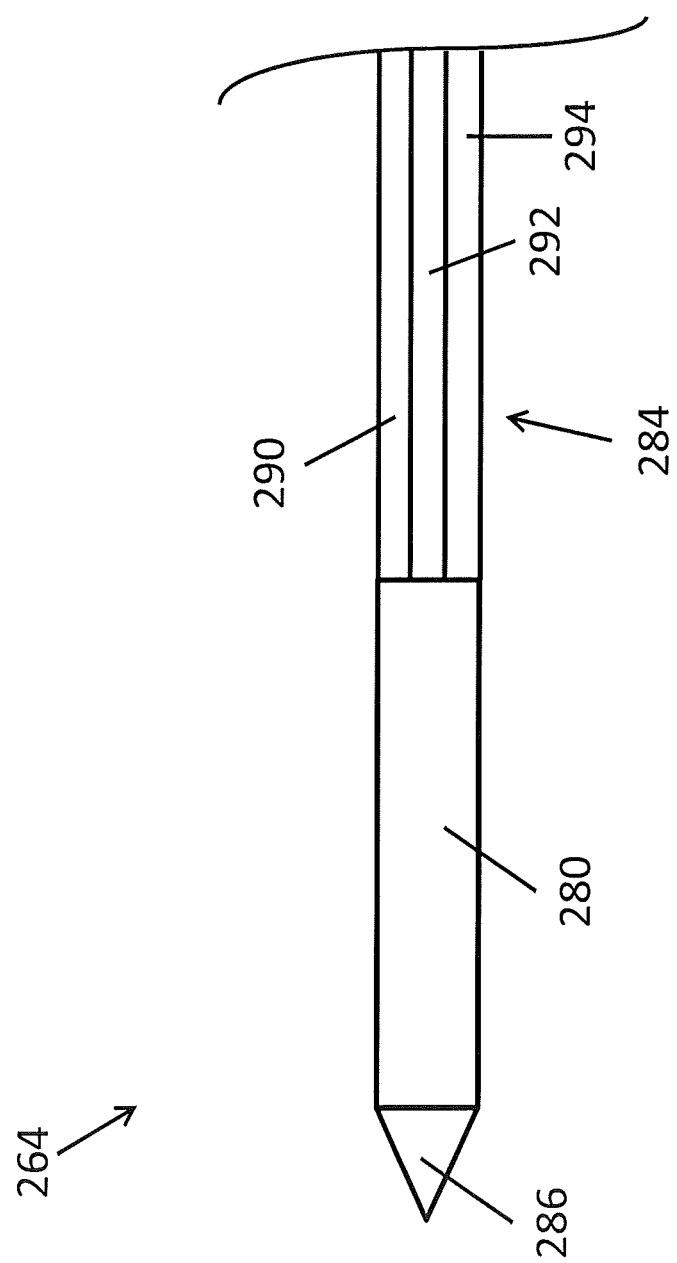
FIG. 9A depicts a top plan view of the blade of FIG. 7, in a substantially straight configuration.
Figure 9B:
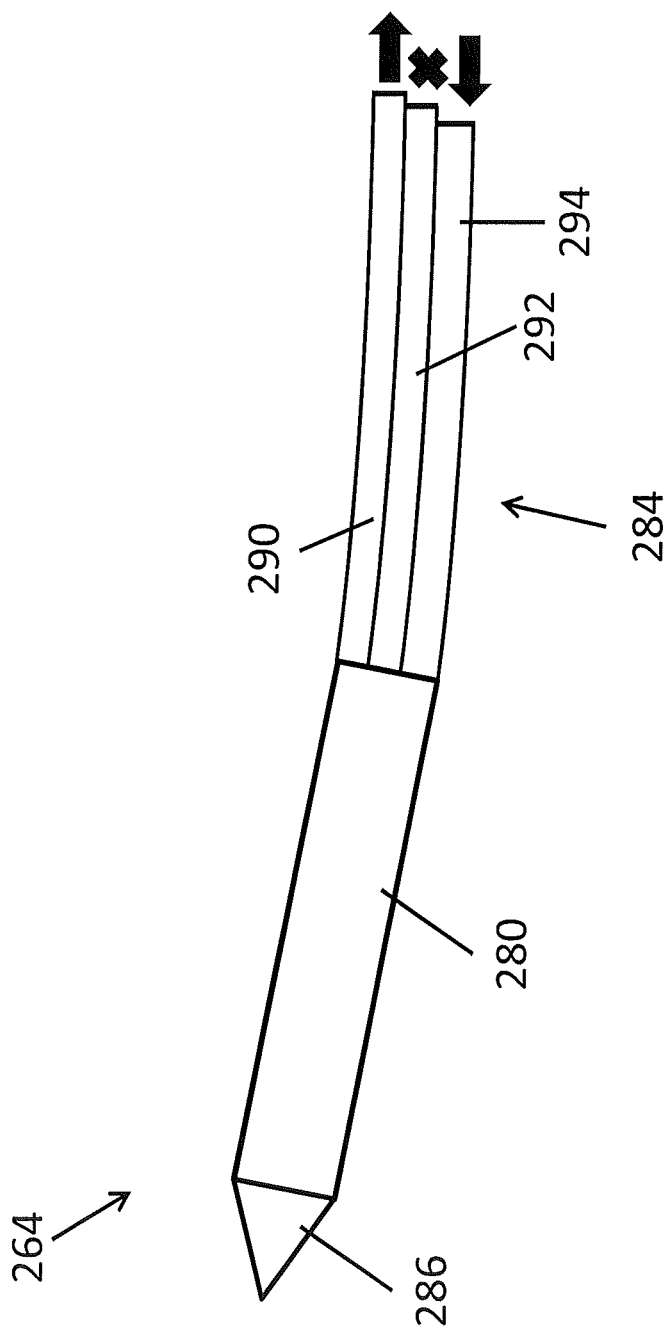
FIG. 9B depicts a top plan view of the blade of FIG. 7, in a substantially bent configuration.

Body (284) of the exemplary version comprises a laminate strip of metal. In particular, body (284) is made of three sheets of metal laminated together. FIG. 9 shows a top view of blade (264) showing body (284) formed by laminate sheets of metal. Body (284) of the exemplary version comprises a first sheet (290), a second sheet (292), and a third sheet (294). It will be understood that while the exemplary version shows body (284) being made of three sheets of metal, any suitable number of sheets may be used. For instance, two sheets, a single sheet, or more than three sheets may be used. First sheet (290), second sheet (292), and third sheet (294) are sandwiched together to form body (284). Furthermore, sheets (290, 292, 294) are pressed together such that they can slide longitudinally relative to one another. In other words, first sheet (290) may slide relative to second sheet (292), and second sheet (292) may slide relative to third sheet (294), as seen in FIG. 9B. In the exemplary version, sheets (290, 292, 294) have an elongated rectangular shape with openings (288) formed therein. Openings (288) are patterned uniformly along blade (254) as seen in FIG. 7. However, it will be appreciated that any positioning of openings (288) along blade (264) may be used as would be apparent to one of ordinary skill in the art. It will further be appreciated that openings (288) along blade (264) may be operable to increase the strength of blade (264) to prevent blade (264) from deforming in the event that blade (264) receives impacts from any direction along blade (264). It will be understood that openings (288) need not be included with sheets (290, 292, 294).

As mentioned above, sheets (290, 292, 294) are operable to slide relative to one another. FIG. 9B shows a top view of blade (264) with head (280) bent to the right (assuming one is looking longitudinally from sheets (290, 292, 294) to edge (286)). As head (280) bends to the right, first sheet (290) retracts proximally while third sheet (294) advances distally. Second sheet (292) maintains a generally constant longitudinal position. It will be understood that the above described motions of sheets (290, 292, 294) are reversed when head (280) is bent to the left. Furthermore, as head (280) bends to the right or left, sheets (290, 292, 294) also curve accordingly to the right or left in addition to sliding relative to one another. Thus, when blade (264) is advanced along end effector (140), edge (286) may encounter the curvature of jaw (142), causing head (280) and sheets (290, 292, 294) to bend in the direction of the curvature. As shown in FIG. 6, jaw (142) bends to the right and as a result, sheets (290, 292, 294) displace and curve in the manner shown in FIG. 9B. It will be appreciated that such bending of head (280) allows blade (264) to advance along jaw (142) using less force as edge (286) is less likely to rub forcefully against the sides of jaw (142) thereby increasing friction.

It will be understood sheets (290, 292, 294) may be constructed of a resiliently deformable material such that in addition to displacing similar to the manner shown in FIG. 9B, sheets (290, 292, 294) may bend such that head (280) may bend even further in relation to sheets (290, 292, 294). Generally speaking, sheets (290, 292, 294) are laterally flexible and longitudinally stiff. As a result, sheets (290, 292, 294) are operable to transmit blade (264) driving forces as sheets (290, 292, 294) are fired along a curved path of jaw (142). In some versions, sheets (290, 292, 294) may have a resiliently flexible construction. For instance, sheets (290, 292, 294) may be biased such that sheets (290, 292, 294) assume a straight configuration or biased to assume a curved configuration. In other versions, it will be understood that sheets (290, 292, 294) may have a non-resiliently flexible construction.

Figure 10:
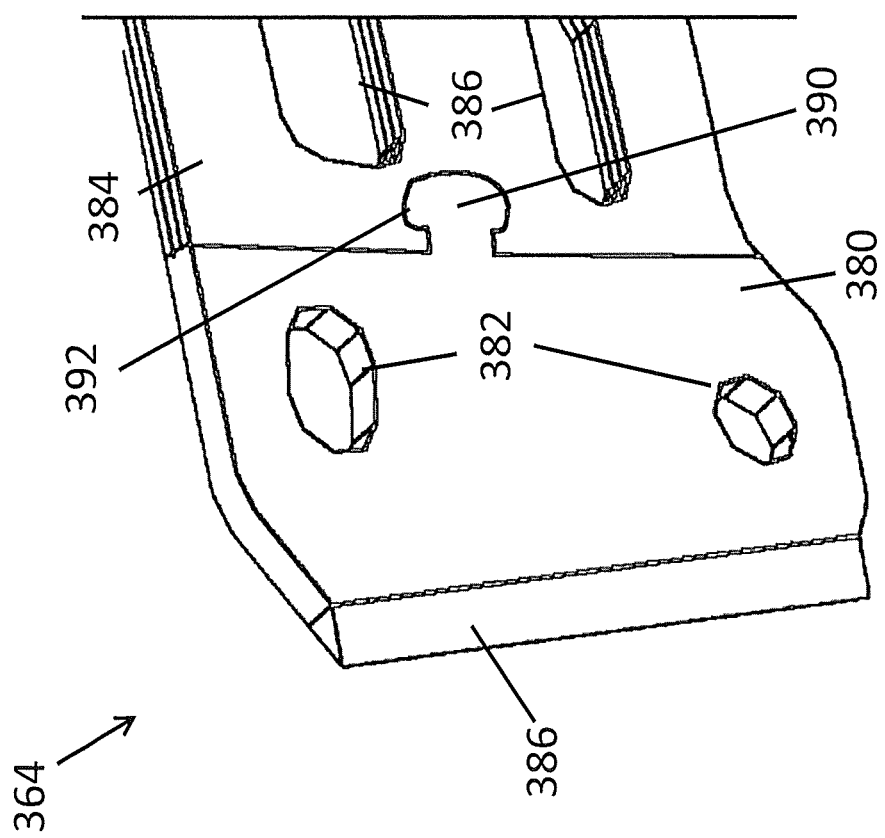
FIG. 10 depicts a perspective view of the head of an alternative exemplary version of a blade.

It will be appreciated that in some instances, it may be desirable to use different heads with blade. Accordingly, it may be desirable to have a head that may be removed from the rest of the blade. FIG. 10 depicts an exemplary blade (364) having a removable head (380). Blade (364) further comprises edge (386) and body (384). Head (380) defines pin holes (382), and body (384) defines openings (386) formed therein. It will be appreciated that blade (364) is substantially similar to blade (264) shown in FIG. 8. Pin holes (382) are configured to receive pins, similar to pins (166) described above. In some versions, the upper pin hole (382) is in the form of a curved oblong slot, enabling the upper pin to slide within pin hole (382) during reversal of translation of blade (364). Such a pin hole (382) and corresponding pin may be constructed an operable in accordance with at least some of the teachings of U.S. patent application Ser. No. 13/692,211, entitled "Surgical Instrument with Secondary Jaw Closure Feature," filed on even date herewith, and published Jun. 5, 2014 (Pub. No. 2014/0151428), the disclosure of which is incorporated by reference herein. In addition or in the alternative, pin holes (382) may be dimensioned to permit their associated pins to rotate or roll relative to and/or within pin holes (382) as blade (364) translates. Such rotation/rolling may reduce the force required to translate blade (364) distally and/or proximally. As another merely illustrative example, pin holes (382) (and/or other features of blade (364)) may be constructed in accordance with at least some of the teachings of U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein.

Head (380) of the exemplary version shown in FIG. 10 comprises a keyed portion (390) operable to couple with a complementary interface (392) of body (384). Keyed portion (390) and interface (392) comprise a half circle shape. However, it will be understood that any suitable shape may be used for keyed portion (390) and interface (392) as would be apparent to one of ordinary skill in the art in view of the teachings herein. For example, keyed portion (390) and interface (392) may have a dovetail, square, diamond, or any other suitable shape. In some versions it will be understood that the connection between keyed portion (390) and interface (392) need not necessarily be mechanical. For instance, in addition or in the alternative, keyed portion (390) and interface (392) may include sensors and an electronic handshake to verify that keyed portion (390) and interface (392) are compatible for engagement. Other suitable mechanisms for joining keyed portion (390) and interface (392) will be apparent to one of ordinary skill in the art in view of the teachings herein. In the exemplary version, keyed portion (390) may be slid into interface (392) or in the alternative, keyed portion (390) may be interferingly pressed or snapped into interface (392). Other suitable ways of joining head (380) and body (384) through keyed portion (390) and interface (392) will be apparent to one of ordinary skill in the art in view of the teachings herein.

It will be appreciated that other heads (not shown) may be used with body (384). Thus, a user may remove head (380) to replace head (380) with an alternative head by engaging the alternative head with interface (392). Similarly, a different body may be used in place of body (384). The configuration of head (380) and body (384) may facilitate the combination of a head (380) formed of one material with a body (384) formed of other materials. By way of example only, head (380) may be formed of spinodal bronze. Head (380) may also be coated with tungsten disulfide, vanadium nitride, and/or other low friction coatings to reduce friction with jaws (142, 144) and/or to reduce friction with pins disposed in pin holes (382).

IV. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
    (a) an end effector comprising
        (i) a first jaw, and
        (ii) a second jaw,
        wherein the first jaw and the second jaw are configured to clamp tissue, wherein the first jaw and the second jaw define a curved path; and
    (b) a blade, wherein the blade comprises:
        (i) a head portion presenting a cutting edge operable to sever tissue clamped between the first jaw and the second jaw, and
        (ii) a body operable to drive the head portion, wherein the body is operable to translate along the curved path defined by the first jaw and the second jaw,
        wherein at least a portion of the blade is precurved such that the blade is resiliently biased to assume a curved configuration and comprises at least two layers of laminate sheets.

2. The apparatus of claim 1, wherein the head portion is approximately 0.5 inches long.

3. The apparatus of claim 1, wherein the curvature of the precurved portion of the blade complements the curvature of the curved path.

4. The apparatus of claim 1, wherein at least a portion of the blade comprises stainless steel coated with tungsten disulfide or vanadium nitride.

5. The apparatus of claim 1, wherein the first jaw comprises a first electrode, wherein the second jaw comprises a second electrode, wherein the first electrode and the second electrode are configured to deliver RF energy.

6. The apparatus of claim 5, wherein the first electrode and the second electrode are configured to activate after the blade has translated along the curved path in the end effector.

7. The apparatus of claim 1, wherein at least a portion the blade comprises spinodal bronze.

8. The apparatus of claim 1, wherein the body defines a plurality of openings along the length of the body portion.

9. The apparatus of claim 1, wherein the body of the blade comprises a laminated set of sheets.

10. The apparatus of claim 9, wherein the sheets are configured to slide in relation to one another.

11. The apparatus of claim 9, wherein the sheets comprise three metal sheets.

12. The apparatus of claim 9, wherein the sheets are flexible.

13. The apparatus of claim 1, wherein the blade includes at least one pin, wherein the at least one pin is configured to travel along the first jaw.

14. The apparatus of claim 13, wherein the blade and the at least one pin are integrally formed.

15. The apparatus of claim 1, wherein the head portion comprises a keyed portion, wherein the body defines an interface, wherein the keyed portion is configured to selectively fit in the interface.

16. An apparatus comprising:
    (a) an end effector comprising
        (i) a first jaw, and
        (ii) a second jaw,
        wherein the first jaw is pivotable relative to the second jaw, wherein the first jaw and the second jaw define a curved path; and
    (b) a blade, wherein the blade comprises:
        (i) a head comprising a proximal portion and a distal portion, wherein the distal portion includes a cutting edge operable to sever tissue captured by the first jaw and the second jaw, and
        (ii) a body coupled to the proximal portion of the head, wherein the body is operable to drive the head, wherein the body is operable to translate along the curved path defined by the first jaw and the second jaw, wherein the body comprises at least two laminate sheets, wherein the at least two laminate sheets are configured to displace in relation to each other in response to the body translating along the curved path.

17. The apparatus of claim 16, wherein the at least two laminate sheets define a plurality of openings along the at least two laminate sheets.

18. The apparatus of claim 16, wherein the head comprises a pre-curved structure.

19. The apparatus of claim 16, wherein the head is in selective communication with the at least two laminate sheets.

20. A blade comprising:
    (a) a plurality of laminate sheets configured to advance longitudinally along an end effector, wherein the laminate sheets are flexible, wherein the laminate sheets are configured to slide relative to each other;
    (b) one or more pins extending transversely relative to the plurality of laminate sheets; and
    (c) a head portion coupled with the plurality of laminate sheets, wherein the head portion is positioned distally in relation to the laminate sheets, wherein the head portion includes a cutting edge distal to the one or more pins, wherein the cutting edge is configured to transect tissue.

* * * * *